United States Patent [19]
Knode

[11] Patent Number: 5,846,079
[45] Date of Patent: Dec. 8, 1998

[54] SINGLE TOOTH DENTAL RESTORATION SYSTEM

[75] Inventor: Helmut Knode, Trier, Germany

[73] Assignee: Implant Innovations, Inc., Palm Beach Gardens, Fla.

[21] Appl. No.: 810,305

[22] Filed: Feb. 28, 1997

Related U.S. Application Data

[60] Provisional application No. 60/012,567 Feb. 29, 1996.

[51] Int. Cl.$^6$ .................................................... A61C 11/00
[52] U.S. Cl. ........................................ 433/213; 433/214
[58] Field of Search ............................... 433/172, 173, 433/174, 175, 176, 214, 213

[56] References Cited

U.S. PATENT DOCUMENTS

| | | |
|---|---|---|
| 4,086,701 | 5/1978 | Kawahara et al. . |
| 4,306,862 | 12/1981 | Knox .................................... 433/77 |
| 4,341,312 | 7/1982 | Scholer .................................. 433/77 |

(List continued on next page.)

FOREIGN PATENT DOCUMENTS

| | | |
|---|---|---|
| 0 442 855 A1 | 8/1991 | European Pat. Off. . |
| 0 657 146 A1 | 6/1995 | European Pat. Off. . |
| 1 291 470 | 10/1972 | United Kingdom . |

OTHER PUBLICATIONS

Richard J. Lazarra, "Managing the Soft Tissue Margin: The Key to Implant Aesthetics", *PP & A*, Jun./Jul. 1993, vol. 5 No. 5, pp. 81–87.
Exhibit A, a drawing of a healing abutment.
Exhibit B, an assembly drawing of a coping and the component drawings which comprise the coping assembly.
Lewis, S.G. et al., *Single Tooth Implant Supported Restorations*, Intl. Jrnl. of Oral & Maxillofacial Implants, vol. 3, No. 1, pp. 25–30, 1988.
Lewis, S. G. et al., *The "UCLA" Abutment*, Intl. Jrnl. of Oral & Maxillofacial Implants, vol. 3, No. 3, pp. 183–189, 1988.
Perri, George et al., *Single Tooth Implants*, CDA Journal, vol. 17, No. 3, pp. 30–33, Mar. 1989.
DIA™ Dental Imaging Associates, Inc., IMPLA–MED The Source, *The Anatomic Abutment System™*, front and back covers, pp. 1–10, Copyright Oct. 1991.
Steri–Oss®, The Future of Implant Dentistry Product Catalog, Feb. 1992, cover and back pages, pp. 7, 14.
Branemark System® SMILINE, Product Catalog Prosthetics, (Nobelpharma) 1991, 24 pages.
Steri–Oss® A Denar Affiliate, The Future of Implant Dentistry, Product Catalog, Sep. 1990, 36 pages.
IMTEC Hexed–Head™ Implant System, Spring 1993 Catalog, IMTEC Corporation®, 15 pages.

(List continued on next page.)

*Primary Examiner*—Cary E. O'Connor
*Attorney, Agent, or Firm*—Arnold, White & Durkee

[57] ABSTRACT

A system for making anatomically correct and aesthetically pleasing dental restorations, including a modeling structure for fashioning a custom-made impression coping and a method of using the model to form said impression coping. A healing abutment used in second stage surgery to form an opening in the gingiva of a dental patient is attached to an implant analog within the model. Impression material is poured into the modeling receptacle around the healing abutment so as to form a model of the patient's gingival layer, including a cavity in the model corresponding to the opening in the patient's gingival layer. A narrow coping shaft is attached to the implant analog within the modeling receptacle, and a modeling material is poured into the cavity and allowed to harden around the narrow coping shaft, thus forming an impression coping with a transmucosal section replicating the size and shape of the healing abutment. The impression coping may thereafter be connected to a dental implant in the patient's jawbone (after removal of the healing abutment) so that an impression may be taken in the usual manner to be used in making a stone model of the surgery site, which in turn may be used in fashioning an artificial tooth.

21 Claims, 4 Drawing Sheets

U.S. PATENT DOCUMENTS

| | | | |
|---|---|---|---|
| 4,758,161 | 7/1988 | Niznick | 433/173 |
| 4,767,331 | 8/1988 | Hoe | 433/213 |
| 4,842,518 | 6/1989 | Linkow et al. | 433/174 |
| 4,850,870 | 7/1989 | Lazzara et al. | 433/174 |
| 4,850,873 | 7/1989 | Lazzara et al. | 433/220 |
| 4,856,994 | 8/1989 | Lazzara et al. | 433/173 |
| 4,955,811 | 9/1990 | Lazzara et al. | 433/173 |
| 4,988,298 | 1/1991 | Lazzara et al. | 433/173 |
| 5,000,685 | 3/1991 | Brajnovic | 433/173 |
| 5,006,069 | 4/1991 | Lazzara et al. | 433/173 |
| 5,015,186 | 5/1991 | Detsch | 433/173 |
| 5,030,096 | 7/1991 | Hurson et al. | 433/173 |
| 5,035,619 | 7/1991 | Daftary | 433/173 |
| 5,040,983 | 8/1991 | Binon | 433/173 |
| 5,071,351 | 12/1991 | Green, Jr. et al. | 433/173 |
| 5,073,111 | 12/1991 | Daftary | 433/173 |
| 5,100,323 | 3/1992 | Friedman et al. | 433/173 |
| 5,135,395 | 8/1992 | Marlin | 433/174 |
| 5,145,371 | 9/1992 | Jörnéus | 433/173 |
| 5,145,372 | 9/1992 | Daftary et al. | 433/173 |
| 5,145,612 | 9/1992 | Carlsson et al. | 433/173 |
| 5,188,800 | 2/1993 | Green, Jr. et al. | 422/23 |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,246,370 | 9/1993 | Coatoam | 433/173 |
| 5,281,140 | 1/1994 | Niznick | 433/172 |
| 5,292,252 | 3/1994 | Nickerson et al. | 433/173 |
| 5,297,963 | 3/1994 | Daftary | 433/172 |
| 5,316,476 | 5/1994 | Krauser | 433/173 |
| 5,334,024 | 8/1994 | Niznick | 433/173 |
| 5,336,090 | 8/1994 | Wilson, Jr. et al. | 433/172 |
| 5,338,196 | 8/1994 | Beaty et al. | |
| 5,368,483 | 11/1994 | Sutter et al. | 433/173 |
| 5,419,702 | 5/1995 | Beaty et al. | 433/214 |
| 5,431,567 | 7/1995 | Daftary | 433/172 |
| 5,433,606 | 7/1995 | Niznick et al. | 433/173 |
| 5,476,383 | 12/1995 | Beaty et al. | 433/214 |
| 5,492,471 | 2/1996 | Singer | 433/172 |
| 5,547,377 | 8/1996 | Daftary | 433/172 |
| 5,564,921 | 10/1996 | Marlin | 433/172 |

OTHER PUBLICATIONS

Interpore International, "IMZ™ Prosthetic Flow Chart", Jul. 1993, 2 sheets.

Impla–Med™ Incorporated, The Source, "Come to the Source. The Choice is Clear." Catalog, Mar. 1991, 16 pages.

Stryker® Dental Implants, "Surgical Flexibility Prosthetic Simplicity" Stryker Universal Hextop Component™, Catalog Data Sheet, undated, 8 sheets.

Stryker® Dental Implants, Price List, Jun. 1, 1993, 46 pages.

Oratronics, Inc., "*Options for Oral Implantology . . . Oratronics Endosseous Tri–Dimensional T–3D Oral Implant Healing System (OIHS)*", 1978, 8 pages.

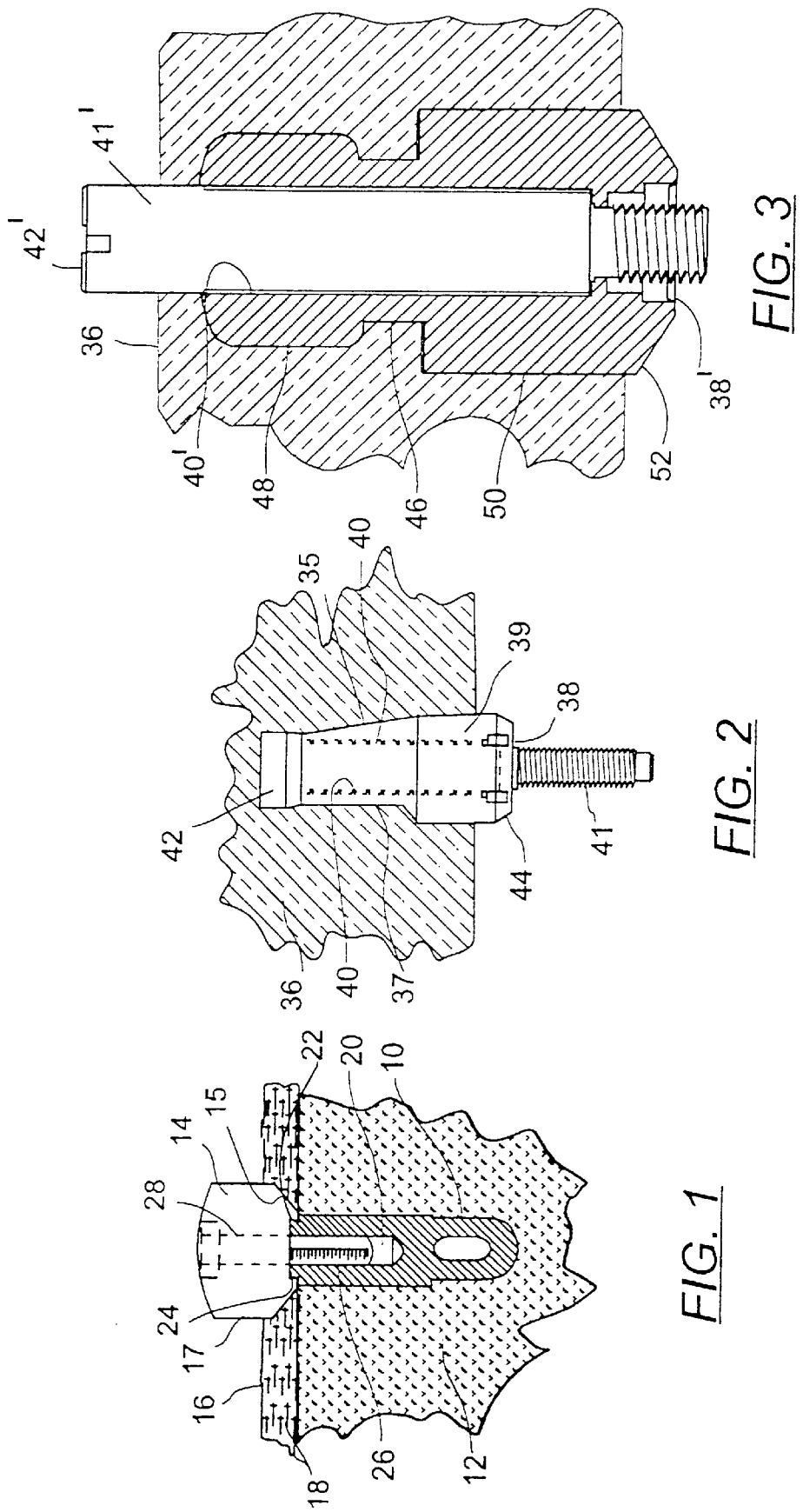

SINGLE TOOTH DENTAL RESTORATION SYSTEM

CROSS REFERENCES TO RELATED APPLICATIONS

This application claims the benefit of priority of provisional U.S. patent application Ser. No. 60/012,567, filed on Feb. 29, 1996.

FIELD OF THE INVENTION

The present invention relates generally to dental restoration systems in which an artificial tooth is fashioned to replace a lost natural tooth and attached to a dental implant structure at the site of the missing tooth. More particularly, the present invention is directed to a set of components and a method of using same to fashion an artificial tooth closely replicating the appearance of a lost natural tooth.

BACKGROUND OF THE INVENTION

Dental implants are becoming an increasingly popular means for restoring lost teeth in wholly or partially edentulous patients. A dental implant typically comprises a threaded titanium cylinder having a length ranging between about 5 mm and 13 mm and a diameter ranging between about 3 mm and 6 mm. The most common type of dental implant now in use has a hexagonal post or boss (commonly called a hex) on its gingival end. The hex of the implant is adapted to anti-rotationally mate with a corresponding hexagonal socket on an artificial tooth or abutment to which the restored tooth is attached.

The restoration of a single tooth typically occurs in two stages. In the first stage, a dental implant in inserted in the jawbone of a dental patient in the location of the natural root of the lost tooth. After the first stage surgery, the implant is left in position in the jawbone, covered by the patient's fleshy gum tissue, for several months until it becomes osseointegrated within the patient's jawbone. Thereafter, in the second stage, the gum tissue is opened to expose an end of the implant, and a healing abutment is attached to the implant until the surrounding gum tissue heals around the abutment. After the gum tissue has healed, the healing abutment is typically removed and the implant is available to support an artificial tooth. The process of fashioning the artificial tooth usually begins with the step of attaching an impression coping to the implant and making a dental impression of the coping and surrounding teeth. The impression is then removed from the patient's mouth so that it may be used to make a stone model of the patient's case.

In one technique using a "pick-up" type impression coping, the coping is automatically "picked up" (i.e. removed from the implant) during removal of the impression material. In another technique using a "transfer" type impression coping, the coping remains attached to the implant during removal of the impression material, but is then removed from the implant by the clinician and "transferred" back into the impression material. In either case, the coping is designed to be positioned within the impression material in the same orientation as it had been positioned in the implant. An implant analog is then attached to the coping and a stone model is made. Thereafter, the artificial tooth is fashioned on the implant analog within the stone model and ultimately removed from the stone model so that it may be attached to the actual implant within the patient's mouth.

One of the most important aspects of a successful restoration is that the restored tooth must closely replicate the appearance of the lost natural tooth with respect to its "emergence profile" (i.e., the portion of the tooth which extends through and emerges from the gums). The aesthetic aspect of the dental restoration is particularly important when a single anterior (i.e. front) tooth is being restored. Nevertheless, an aesthetically pleasing or anatomically correct emergence profile is difficult to achieve with dental restorative components known in the art. Part of the reason for this is that components such as healing abutments and impression copings are typically not dimensioned to perfectly replicate the dimensions of a natural tooth where it emerges from the gum. For example, natural teeth generally have a non-round shape where they emerge from the gum comprising a shorter dimension and a longer (mesial-distal) dimension. In contrast, many of the healing abutments known in the art have a circular cross section, typically with a diameter of about 4.5 mm to 8.0 mm to approximate the mesial-distal dimension of the tooth being replaced. At the same time, many of the impression copings of the prior art are all one size, about 4.5 mm in diameter. As a result, a gap is left in the gingiva, around the impression coping, and impression material fills this gap when an impression is taken. The gingiva also tend to collapse into this gap, resulting in less than accurate replication of the conditions in the patient's mouth. As a further consequence of these problems, it is difficult to make soft issue models accurately. Stone models replicate these errors, and this requires technicians to shape the stone manually to comply with the conditions in the patient's mouth, or risk producing a crown with an inaccurate emergence profile or crown to abutment margin that is misplaced.

In view of the above-described problems, there is a need for a dental restoration system using components which closely replicate the dimensions of natural teeth, to facilitate the fashioning of artificial teeth having emergence profiles closely replicating those of lost natural teeth. The present invention is directed to addressing this need by providing new surgical and laboratory components, and new procedures, to further improve the art of making anatomically correct and aesthetically pleasing dental restorations.

SUMMARY OF THE INVENTION

In accordance with one aspect of the present invention, there is provided a modeling structure for use in fashioning an impression coping to be used in a single-tooth dental restoration system. The modeling structure comprises a receptacle including a base portion and a sidewall portion within which a flowable dental impression material may be poured. A socket formed within the base portion of the receptacle is adapted to receive an implant or implant analog therein, such that a proximal end of the implant or implant analog is accessible through an opening in the base portion of the receptacle. The proximal end is adapted to receive a dental restorative component thereon, such as a healing abutment or impression coping.

In accordance with another aspect of the present invention, there is provided a method of using the modeling structure described above to form an impression coping from a healing abutment. The healing abutment corresponds in size and shape to the trans-tissue portion of a natural tooth and is used to form an opening in the gingiva of a dental patient in second stage surgery. A first step of the method is to attach the healing abutment to the implant or implant analog disposed within the modeling receptacle such that the healing abutment is positioned above the base portion and within the sidewall portion of the modeling receptacle. Impression material is then poured into the modeling receptacle to a desired depth surrounding the healing abutment so as to form a model of the patient's gingival layer. The healing abutment is then removed from the model to define a cavity in the model corresponding in size and shape to the healing abutment. Next, a narrow coping shaft is attached to the artificial root within the modeling receptacle. One end of the narrow coping shaft includes an interlocking member adapted to interconnect with the artificial root. Then, a modeling material is poured into the cavity and allowed to harden around the narrow coping shaft, thereby forming a transmucosal section of a custom-made impression coping which replicates the size and shape of the healing abutment. The custom-made impression coping may thereafter be connected to a dental implant in the patient's jawbone (after removal of the healing abutment) so that an impression may be taken in the usual manner to be used in making a stone model of the surgery site, which in turn may be used in fashioning an artificial tooth.

BRIEF DESCRIPTION OF THE DRAWINGS

The foregoing and other advantages of the invention will become apparent upon reading the following detailed description and upon reference to the drawings in which:

FIG. 1 is a longitudinal section that shows an implant installed in a bone with a healing abutment in place;

FIG. 2 is a longitudinal section that shows a transfer coping used to make an impression;

FIG. 3 is a longitudinal section that shows a pick-up coping used to make an impression;

FIG. 4b is a top view of the healing abutment shown in FIG. 4a;

FIG. 5b is a top view of the modeling structure, healing abutment and impression material shown in FIG. 5a;

Figure 5B:
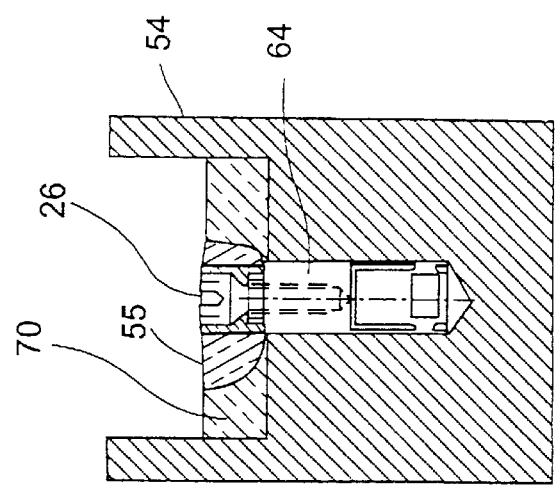

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DESCRIPTION OF SPECIFIC EMBODIMENTS

Turning now to the drawings and referring initially to FIG. 1, there is shown a dental implant 10 installed in a section of a patient's jawbone 12 at the site of a missing tooth. The dental implant 10 serves as an artificial root on which an artificial tooth will be placed at the completion of the restoration. The dental implant 10 is typically placed in the jawbone 12 during "first stage" surgery, after which it is left in position, covered by the patient's fleshy gum tissue 18, for several months until it becomes osseointegrated with the jawbone 12. Thereafter, in "second stage" surgery, the gum tissue 18 is opened to expose an end of the implant 10, and a healing abutment 14 is attached to the implant for the purpose of allowing the surrounding gum tissue 18 to heal in the shape of the abutment. In order to provide for an emergence profile replicating that of a natural tooth, the healing abutment 14 will preferably closely approximate the size and shape of the trans-tissue portion of a natural tooth.

U.S. patent application Ser. No. 08/527,508, assigned to the assignee of the present invention and incorporated herein by reference, discloses a set of prefabricated healing abutments from which the healing abutment 14 may be selected, together with matching impression copings, each being shaped and sized for use in preparing restorations for particular types of teeth such as, for example, molars, premolars, bicuspids and incisors. The prefabricated impression copings in this system are thus designed to fit perfectly within the gingival aperture formed by an associated prefabricated healing abutment, so that an impression made with the coping may thereafter be used to fashion an artificial tooth having a natural-looking emergence profile. The present invention provides an alternative system in which impression copings are "custom-made" to fit perfectly within the gingival aperture formed by an associated healing abutment. Preferably, the associated healing abutment will also be custom-made in order to more closely approximate the emergence profile of a natural tooth, but it will be appreciated that the present invention may be utilized with either custom-made or prefabricated healing abutments.

At any rate, whether custom-made or prefabricated, the healing abutment 14 shown in FIG. 1 includes a tapered transmucosal section 15 extending from the end of the implant toward an outer surface 16 of the surrounding gingiva 18, beyond which walls 17 of the abutment extend vertically. A portion of the vertical walls 17 may be immersed in the gum tissue, below the outer surface 16, together with the tapered section 15. The implant 10 has an internally threaded bore 20, surrounded at its gingival opening by a non-round boss 22, the external cross section of which typically is hexagonal. The healing abutment 14 has a corresponding non-round socket 24 enveloping the boss 22. Alternatively, as will be appreciated by those skilled in the art, the implant 10 and abutment 14 may be interconnected by means of a non-round socket on the implant and a corresponding non-round boss on the abutment. In the illustrated embodiment, a through-bolt 26 passes through an axial bore 28 in the healing abutment to further secure the abutment to the implant, as is well known in the art.

FIG. 2 shows a transfer coping 35 of a kind used to take impressions, buried in an impression material 36. The essential structure of this impression coping is described and claimed in U.S. Pat. No. 4,955,811, which is owned by the assignee of the present invention. This impression coping has a flat surface 37 for locating it non-rotationally in the impression material. A hexagonal socket 38 in its base 39 fixes it non-rotationally on the implant 10. A bolt 41 with an expanded head 42 extends through an axial bore 40 to attach the impression coping 35 to the implant 10 and hold the coping 35 in the impression material. For the purposes of the present invention, the impression coping has a tapered section 44 at its end surrounding the socket 38 that replicates in size and shape the tapered transmucosal section 15 of the healing abutment, such as healing abutment 14 shown in FIG. 1. As shown in FIG. 2, a portion of the base 39 emerges from the impression material 36, together with the tapered section 44. Preferably, as described in relation to the healing abutment of FIG. 1, the base 39 will be contoured to mimic the natural cross section of the tooth being replaced.

FIG. 3 shows a pick-up coping 46 buried in an impression material 36'. This impression coping has a non-round head portion 48 for anchoring the coping non-rotationally on the implant, if desired, an axial through bore 40' and a bolt 41' passing through this bore to attach the impression coping to the implant. The proximal end 42' of the bolt has no expanded head on it for the reason that in use when an impression is taken, this end of the bolt extends through a hole in the impression tray (not shown). When the impression material has set up in the tray, the bolt 41' is unscrewed from the implant by accessing its proximal end 42' from the outside, and the tray and the coping 46 remains in (is "picked up" by) the impression material, being anchored therein by its expanded head 48. For the purposes of this invention, the pick up coping 46 functions like the transfer coping 35 of FIG. 2. Thus, the base 50 and tapered section 52 of the pick-up coping 46 will preferably replicate the size and shape of the healing abutment used in second stage surgery.

Now turning to FIG. 4a, there is depicted a modeling structure 54, with an associated healing abutment 55 and through-bolt 26 shown exploded, which may be used to fashion a custom-made pick-up coping or transfer coping according to one embodiment of the present invention As will be described in detail hereinafter, the impression coping made from the modeling structure 54 will have a trans-tissue region which "perfectly" replicates the size and shape of the healing abutment used in second stage surgery. The modeling structure 54 consists of a receptacle 56 formed between a base portion 58 and a sidewall portion 60 which is adapted to receive a flowable dental impression material. A socket 62 formed within the bottom of the modeling structure 54 is designed to receiving an implant analog 64 therein. The implant analog 64 has a non-round boss 68 and internally threaded bore 20 corresponding to those of the actual implant 10 (FIG. 1). The implant analog has a proximal end 66 accessible from above the socket which is available to support a dental restorative component with a corresponding non-round socket, such as healing abutment 55. Alternatively,the implant analog 64 may be equipped with a non-round socket for attachment to a corresponding non-round boss on a respective dental restorative component. Moreover, it will be appreciated that the implant analog 64 may be replaced with an actual implant duplicating the implant 10 shown in FIG. 1.

Figure 4B:
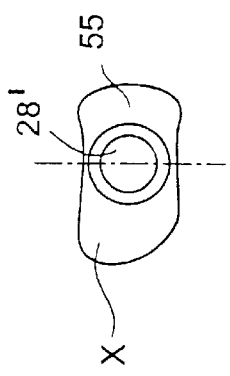

FIG. 4b shows a top view of the healing abutment 55. As can be observed from FIGS. 4a and 4b, the healing abutment 55 has an asymmetrical shape, designed to approximate the contours of the trans-tissue portion of a natural tooth. Preferably, the healing abutment 55 is custom-made to "perfectly" match the emergence profile of a natural tooth, but it will be appreciated that other healing abutments may be used, such as the symmetrical healing abutment 14 shown in FIG. 1 or any suitable healing abutment known in the art. Similar to the healing abutment 14 of FIG. 1, the healing abutment 55 shown in FIGS. 4a and 4b includes an axial bore 28' within which a through-bolt 26' passes to secure the abutment to the implant, as is known in the art, and further includes a hexagonal socket 24' for non-rotational attachment to the corresponding hexagonal boss 68 on the implant analog.

Figure 5A:
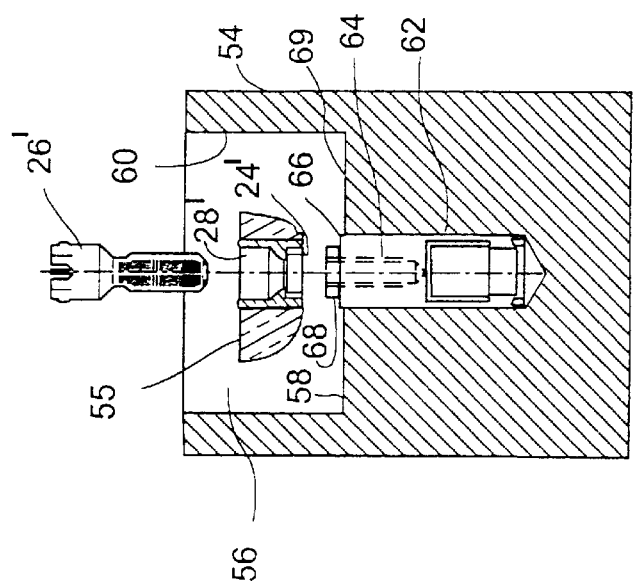
FIG. 5a is a side-sectional view of the modeling structure of FIG. 4 after impression material has been poured into the modeling structure around the healing abutment.
Figure 4A:
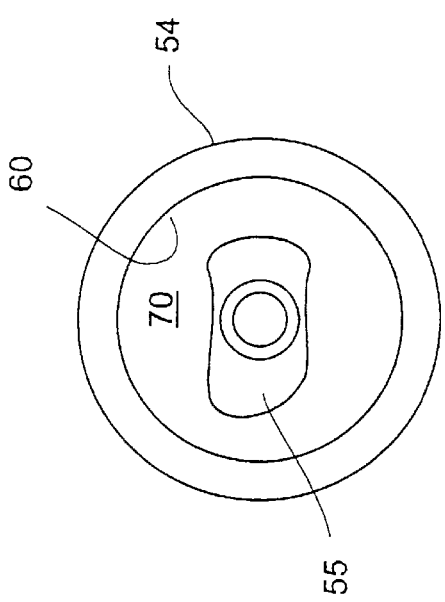
FIG. 4a is a side-sectional view of a modeling structure, with associated healing abutment and through-bolt shown exploded, which may be used to fashion the pick-up coping of FIG. 3 according to one embodiment of the present invention.

Now turning to FIGS. 5a and 5b, there is shown the healing abutment 55 of FIGS. 4a and 4b attached to the implant analog 64 within the modeling structure 54 after impression material 70 has been introduced into the modeling structure 54 to a desired thickness around the healing abutment 14. The impression material 70 flows around and under the healing abutment 55 so as to form an impression 70 extending from around the healing abutment 55 to the sidewalls 60 of the modeling structure 54. As shown in FIG. 5a, the impression 70 thereby comprises a model of the patient's gingiva as it would appear with the healing abutment 55 attached to the implant. As shown in FIG. 5b, the sidewalls 60 of the modeling structure 54 have a circular cross-section, but it will be appreciated that neither the cross-sectional shape of the sidewalls 60 nor the shape of the healing abutment 55 is material to the present invention.

After the impression 70 has been formed, the healing abutment 55 may be removed and installed on the actual implant in the patients jawbone, similar to the healing abutment 14 shown in FIG. 1, causing the gum tissue (mucosa) overlying the implant to heal in the reverse-shape of the healing abutment 55 and forming in the mucosa an aperture surrounding and exposing the gingival end of the implant. Typically, the healing abutment 55 is affixed to the implant in the second stage of a two-stage procedure, after the implant has osseointegrated with the patient's jawbone. Alternatively, however, the healing abutment 55 may be attached to the implant immediately after the implant is installed in the jawbone so that the mucosa heals to the specified shape at the same time the implant is osseointegrating with the jawbone. The healing abutment 55 can then be left in the patient's mouth until the soft (gingival) tissues have matured and the replacement tooth is ready to be installed on the implant.

Figure 6:
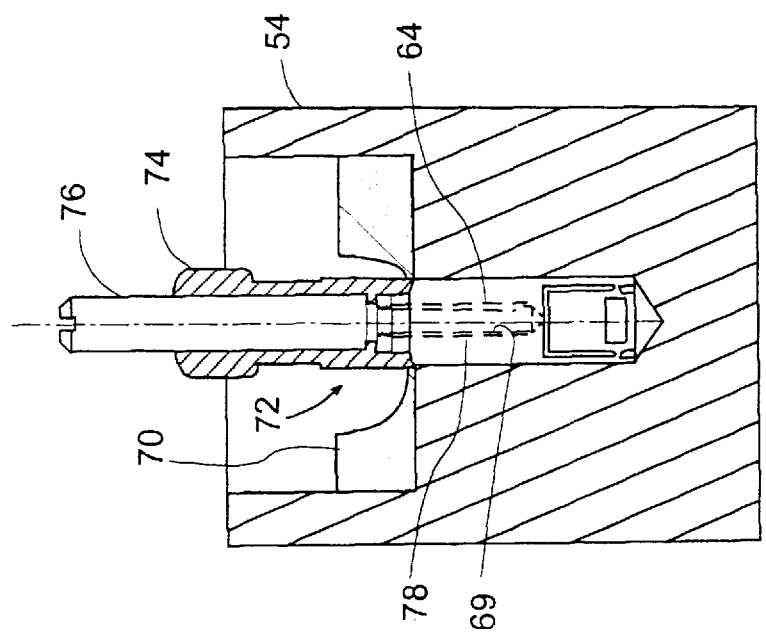
FIG. 6 is a side-sectional view of the modeling structure of FIGS. 4 and 5 portraying a cavity formed by the removal of the healing abutment of FIGS. 4 and 5 and a narrow coping shaft disposed within the cavity.

As can be seen in FIG. 6, after the healing abutment 55 is removed from the impression material 70, a cavity 72 identical to the aperture formed in the mucosa is formed in the impression material 70 surrounding and exposing the gingival end of the implant analog 64. Both the cavity 72 and the aperture in the mucosa will correspond in size and shape to the healing abutment 55, which preferably corresponds to the size and shape of the trans-tissue portion of a natural tooth. An impression coping shaft 74 having a width narrower than the cavity 72 is attached to the implant analog 64 so that it extends above the implant analog 64 and through the cavity 72. Preferably, the impression coping shaft 74 is attached to the implant analog 64 in the same manner as the healing abutment in FIG. 5a. More specifically, the narrow coping shaft 74 is indexed non-rotationally with the implant analog 64 by interconnection of a hexagonal socket on the coping shaft with a corresponding hexagonal boss on the implant analog, and is tightened onto the implant analog 64 by means of a screw-post 76 having a threaded end portion 78 engaged within the threaded bore 69 of the implant analog 64. As illustrated in FIG. 6, the narrow coping shaft 74 comprises a known form of pick-up coping, similar to that of FIG. 3, but it will be appreciated that the present invention may also be used to fashion other forms of impression copings known in the art, including transfer copings similar to that shown in FIG. 2.

Figure 7:
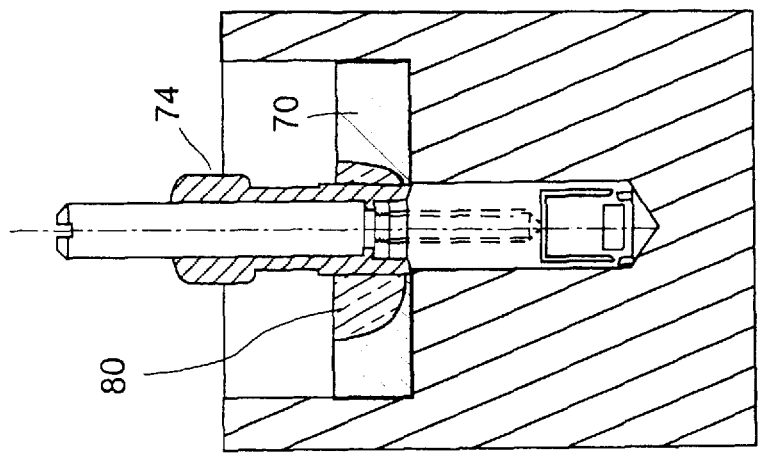
FIG. 7 is a side-sectional view of the modeling structure, cavity and narrow coping shaft of FIG. 6 after modeling material has been poured into the cavity to form a transtissue portion on said narrow coping shaft.

As shown in FIG. 7, an acrylic modeling material 80 is then placed around the coping shaft 74 in the cavity 72 formed in the impression material 70, where it hardens on the coping shaft 74 to the same unique shape as the original healing abutment 55. The coping shaft 74 and modeling material 80 thereby become conjoined to form a pick-up impression coping, with the modeling material 80 forming a trans-tissue portion of the impression coping which corresponds in size and shape to the trans-tissue portion of a natural tooth. The impression coping may thereafter be used to make an impression of the site of the missing tooth in the usual manner. The impression material and impression coping may then be used in the laboratory in the usual manner to make a model in which the unique shape of the trans-tissue region of the gingiva is reproduced, on which to make the artificial tooth.

It will be appreciated that the modeling material 80 used to form the trans-tissue portion of the impression coping is not limited to acrylics, but may comprise any of several alternative materials known in the art, so long as the selected material will harden and conjoin to the coping shaft 74 in the shape of the cavity 72. The selected material must also be capable of being introduced into the cavity 72 without deforming or adhering to the impression material 70. If desired, the coping shaft 74 may incorporate a knurled or irregular outer surface, or any other suitable means known in the art, to more readily accept and bond with the modeling material 80.

Figure 8:
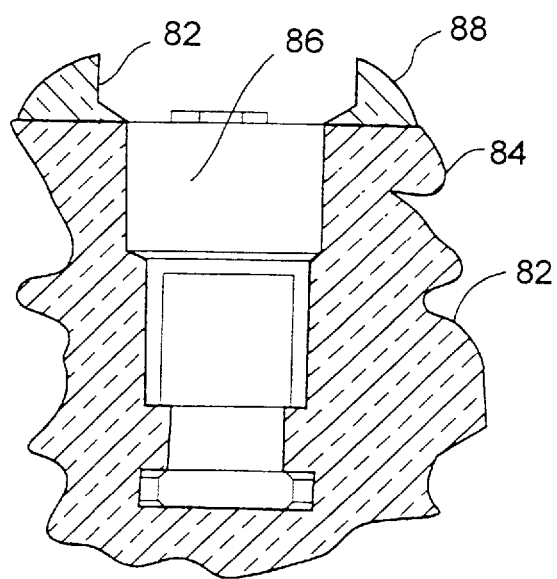
FIG. 8 is a cross-sectional view of a soft tissue model upon which an artificial tooth may be fashioned according to one embodiment of the present invention.

The model may comprise any suitable model known in the art, but preferably the model is one having a resilient gingiva-replicating material providing an artificial soft tissue in which the uniquely-shaped opening of the original impression material is faithfully duplicated. Such a soft-tissue model is shown in FIG. 8, designated generally by reference numeral 82. The soft-tissue model 82 includes a stone foundation 84 rigidly holding an implant replica 86. A soft tissue layer 88, which replicates the human gingiva 18 (FIG. 1), overlies the stone part. This layer can be made of any suitable plastics or rubber-like material having physical properties such as softness and elastically that resemble the physical properties of human gum tissue. Certain silicone based rubber and plastics materials are suitable, preference being given to those that can be fabricated from a soft flowable state. The advantage of the soft-tissue model 82 is that the laboratory technician can manipulate the model exactly as the dentist manipulates the patient's gingiva.

While particular embodiments and applications of the present invention have been illustrated and described, it is to be understood that the invention is not limited to the precise construction and compositions disclosed herein and that various modifications, changes, and variations will be apparent from the foregoing descriptions without departing from the spirit and scope of the invention as defined in the appended claims.

What is claimed is:

1. A modeling structure for use in a single-tooth dental restoration system, said modeling structure comprising:

a receptacle for receiving a flowable dental impression material, said receptacle including a base portion and a sidewall portion, said base portion having an opening therein defining a socket for receiving a dental implant structure, and means substantially replicating the gingival aspect of a dental implant disposed substantially within said socket, a proximal end of said replicating means being accessible through said opening in the base portion of said receptacle, said proximal end being adapted to receive a dental restorative component thereon.

2. The modeling structure of claim 1 wherein the dental implant structure comprises an implant analog.

3. The modeling structure of claim 1 wherein said socket opens into the bottom of said receptacle.

4. A modeling structure for use in a single-tooth dental restoration system comprising:

a receptacle for receiving a flowable dental impression material, said receptacle including a base portion and a sidewall portion, said base portion having an opening therein defining a socket;

a dental implant structure disposed substantially within said socket, a proximal end of said dental implant structure being accessible through said opening in the base portion of said receptacle, said proximal end adapted to receive a dental restorative component thereon.

5. The modeling structure of claim 4 wherein a healing abutment is connected to the proximal end of said dental implant structure, said healing abutment being positioned above said base portion and within said sidewall portion of said receptacle.

6. The modeling structure of claim 5 wherein said healing abutment substantially corresponds in size and shape to the trans-tissue portion of a natural tooth.

7. The modeling structure of claim 6 wherein a body of dental impression material is set up within said receptacle, said impression material surrounding the sides of said healing abutment and in contact with said sidewall portion.

8. The modeling structure of claim 4 wherein a body of impression material is set up within said receptacle, said impression material forming a model of gingivaadjacentto an implant site, said model including a cavity above said dental implant structure corresponding in size and shape to the trans-tissue portion of a natural tooth.

9. The modeling structure of claim 8 wherein an impression coping is connected to the proximal end of said dental implant structure, said impression coping including a trans-tissue portion formed within said cavity and corresponding in size and shape to the trans-tissue portion of a natural tooth.

10. The combination of claim 9 wherein said impression coping is a pick-up coping.

11. A set of dental components for use with a dental root means fixed in a site with an overlying gingiva layer having an opening to the root means, said set comprising:

a healing member for forming said opening in said gingiva;

means to attach said healing member to said root means;

an impression coping having a trans-tissue portion of the same size and shape as said healing member so as to fit fully into said opening in place of said healing member, part of said trans-tissue portion being made of modeling material; and means to attach said impression coping to said root means with said trans-tissue portion fitted into said opening.

12. The set of dental components according to claim 11 wherein said impression coping is a pick-up coping.

13. The set of dental components according to claim 11 wherein said healing member has a unique size and shape corresponding to the trans-tissue portion of a natural tooth.

14. An impression coping for use in fabricating a model of a patient's edentulous jawbone site containing root means with an overlying gingiva layer having an opening to the root means formed from a healing member, said impression coping comprising:

a transmucosal portion having a size and contour replicating that of said healing member, part of said transmucosal portion being made of modeling material, said transmucosal portion being adapted to fit within said opening formed from said healing member;

an impression portion adjacent to the transmucosal portion for extending into impression material; and means for fastening said impression coping to the root means.

15. The impression coping of claim 14 wherein said impression coping is a transfer coping.

16. The impression coping of claim 14 wherein said impression coping is a pick-up coping.

17. The impression coping of claim 14 wherein said healing member has a unique size and shape corresponding to the trans-tissue portion of a natural tooth.

18. The impression coping of claim 14 wherein said impression coping has an elongated body with a through bore for passage of fastening means to attach the impression coping to the root means.

19. A method of fabricating a model of a patient's edentulous jawbone site containing root means with an overlying gingiva layer having an opening to the root means, said method comprising the steps of:

attaching a healing abutment to a gingival end of said root means, said healing abutment corresponding in size and shape to the trans-tissue portion of a natural tooth, said opening in said gingival layer thereafter conforming to the size and shape of said healing abutment;

placing a root means analog into a socket formed in the bottom of a modeling receptacle, a body portion of said root means analog being disposed substantially within said socket, a proximal end of said root means analog being accessible through an opening into said socket at a base portion of said modeling receptacle;

attaching said healing abutment to said proximal end of said root means analog such that said healing abutment is positioned above said base portion and within a sidewall portion of said modeling receptacle;

pouring an impression material into said modeling receptacle to a desired depth surrounding said healing abutment so as to form a model of said gingiva layer;

removing said healing abutment from said model of said gingiva layer to define a cavity in said model corresponding in size and shape to said healing abutment;

attaching an impression coping to the proximal end of said root means analog, said impression coping including a narrow impression portion extending through said cavity and having a width substantially smaller than said cavity;

pouring a modeling material into said cavity and allowing it to harden around said impression coping so as to form a modified impression coping having a transmucosal portion replicating the size and shape of said healing abutment;

removing said modified impression coping from said model and attaching said impression coping to said root means;

taking a dental impression of said patient's jawbone site with said modified impression coping in place; and using said dental impression to make a stone model of the patient's jawbone site.

20. A method of fabricating an impression coping for use in dental restorative surgery from a healing abutment adapted to form an opening in a patient's gingival layer corresponding in size and shape to the trans-tissue portion of a natural tooth, said method comprising the steps of:

attaching said healing abutment to an artificial root means disposed within a modeling receptacle such that said healing abutment is positioned above a base portion and within a sidewall portion of said modeling receptacle;

pouring an impression material into said modeling receptacle to a desired depth surrounding said healing abutment so as to form a model of said patient's gingival layer;

removing said healing abutment from said model to define a cavity in said model corresponding in size and shape to said healing abutment;

attaching a narrow coping shaft to said artificial root means within said modeling receptacle, one end of said narrow coping shaft including an interlocking member adapted to connect to either of said root means and said artificial root means, said narrow coping shaft extending through said cavity and having a width smaller than said cavity; and pouring a modeling material into said cavity and allowing it to harden around said narrow coping shaft so as to form a transmucosal section replicating the size and shape of said healing abutment, said impression coping being defined by the combination of said narrow coping shaft and said transmucosal section.

21. A method of fabricating an impression coping for use in dental restorative surgery, said method comprising the steps of:

attaching a narrow coping shaft to an artificial root means disposed within a modeling receptacle, said narrow coping shaft extending through a cavity formed in said modeling receptacle replicating a gingival aperture formed at an implant site; and pouring a modeling material into said cavity and allowing it to harden around said narrow coping shaft so as to form a transmucosal section replicating that of a natural tooth, said impression coping being defined by the combination of said narrow coping shaft and said transmucosal section.

* * * * *